United States Patent [19]

Fearnot et al.

[11] Patent Number: 5,005,574

[45] Date of Patent: Apr. 9, 1991

[54] TEMPERATURE-BASED, RATE-MODULATED CARDIAC THERAPY APPARATUS AND METHOD

[75] Inventors: Neal E. Fearnot; Merry L. Evans, both of West Lafayette, Ind.

[73] Assignee: Medical Engineering and Development Institute, Inc., West Lafayette, Ind.

[21] Appl. No.: 442,224

[22] Filed: Nov. 28, 1989

[51] Int. Cl.$^5$ ............................................. A61N 1/362
[52] U.S. Cl. ............................................. 128/419 PG
[58] Field of Search ................................. 128/419 PG

[56] References Cited

U.S. PATENT DOCUMENTS

| | | | |
|---|---|---|---|
| 3,867,950 | 2/1975 | Fischell | 128/419 P |
| 4,436,092 | 3/1984 | Cook et al. | 128/419 PG |
| 4,543,954 | 10/1985 | Cook et al. | 128/419 PG |
| 4,719,920 | 1/1988 | Alt et al. | 128/419 PG |
| 4,803,987 | 2/1989 | Calfee et al. | 128/419 PG |

FOREIGN PATENT DOCUMENTS 2609365 9/1977 Fed. Rep. of Germany.

OTHER PUBLICATIONS

Fearnot, et al., "A Review of Pacemakers the Physiologically Increase Rate: The DDD and Rate-Responsive Pacemakers," *Progress in Cardiovascular Diseases* 29(2):145-164, 1986.

Csapo, et al., "Autoregulation of Pacemaker Rate by Blood Temperature," presented at VIII Worlds Congress of Cardiology, Tokyo, Japan, Sep. 17-23, 1978.

Sellers, et al., "Central Venous Temperature Profiles for a Pacemaker Algorithm," *Pace* Mar.-Apr. 1985, 8:294.

Evans, et al., "Evaluation of the Pacing Rate Response to Treadmill Exercise Using Computer Simulation of a Temperature-Based, Rate-Adaptive Algorithm," *Medical Instrumentation*, 22(4):182-188, Aug. 1988.

Primary Examiner—William E. Kamm
Assistant Examiner—Scott M. Getzow
Attorney, Agent, or Firm—Richard J. Godlewski

[57] ABSTRACT

A temperature-based, rate-modulated cardiac pacemaker having means for variably controlling the stimulation rate of the heart according to multiple temperature characteristics of the blood referenced to multiple moving baseline temperatures. A target rate is periodically calculated by obtaining a weighted sum of the following rate components: (1) the magnitude of a decrease in temperature below resting temperature, a first moving baseline, (2) the magnitude of an increase in temperature above a local minimum temperature, a second moving baseline, (3) the magnitude of an increase in the resting baseline above a daily minimum temperature, a third moving baseline, and (4) the absolute value of the rate of change of temperature. The resting temperature is preferably calculated over a longer interval than the local minimum temperature but a much shorter interval than the daily minimum temperature. A positive rate of change of temperature is distinguished from a negative rate of change of temperature and is used differently in the calculation of target rate. The target rate is not directly applied as the new pacing rate but is instead averaged with the previous rate in order to provide smoother transitions between pacing rates. An intermediate rate limit is included in addition to lower and upper rate limits, and rank filtering is employed in the determination of rate components.

73 Claims, 2 Drawing Sheets

TEMPERATURE-BASED, RATE-MODULATED CARDIAC THERAPY APPARATUS AND METHOD

BACKGROUND OF THE INVENTION

The present invention relates to rate-modulated cardiac therapy devices, and, more particularly, to temperature-based, rate-modulated cardiac therapy devices.

Rate-modulated pacemakers, also known as rate-responsive or rate-adaptive pacemakers, stimulate cardiac activity, generally on demand, at a rate determined at least in part by a sensed physiological parameter indicative of required cardiac output. A healthy heart responds to exercise and stress by increasing cardiac output through increased heart rate and stroke volume, and rate-modulated pacemakers more closely approximate this natural response by automatically varying heart rate to meet metabolic demand. Such pacemakers represent a significant advance over early pacemakers, which paced the heart at a single, constant rate, typically near 70 beats per minute. Some patients dependent on fixed-rate pacemakers exhibit limited exercise tolerance because the natural increase in heart rate associated with exercise is not present. While the myocardium is sometimes healthy enough to increase cardiac output by increasing stroke volume, not all patients have adequate response with stroke volume increases alone. Increasing the pacing rate during exercise significantly increases cardiac output and, consequently, exercise tolerance.

Because of its potential in cardiac care, rate modulation is the subject of extensive, ongoing research. A number of biologic parameters have been proposed as indicators of the onset and degree of exercise, including venous pH, Q-T interval, respiratory rate, body motion, stroke volume, venous oxygen saturation, evoked electrogram analysis, pre-ejection period, pressure, and temperature. A review of the clinical experience and basic research in this area is found in Fearnot et al., "A Review of Pacemakers that Physiologically Increase Rate: The DDD and Rate-Responsive Pacemakers," *Progress in Cardiovascular Diseases* 29(2):145-164, 1986. Each proposed parameter has both advantages and disadvantages for control of pacing rate. Problems with sensitivity, accuracy, and transducer reliability and power consumption impede the practical implementation of some of these techniques. Moreover, optimal pacemaker response is difficult to attain because physiological parameters which vary in response to exercise and stress often exhibit similar variations in response to other conditions not affecting cardiac output requirements. Blood temperature, for example, is affected by factors other than metabolic activity, such as environmental ambient temperatures encountered during swimming, bathing and other activities, the temperature of ingested food and drink, changes in posture, and fever. Algorithms capable of differentiating between certain true and false indications of exercise are difficult to design because responses to many conditions vary widely from patient to patient. Furthermore, algorithm efficacy is difficult to verify, particularly in human tests, and an algorithm designed to solve one problem may actually introduce others.

It has long been known on a qualitative level that a relationship exists between some body temperatures and heart rate, but it was not until the mid-1970s that attempts were made to modify pacemaker pulse generator circuitry to respond in even a primitive fashion to temperature. Only in this decade has quantitative analysis of the temperature-rate relationship been performed in an effort to derive and implement accurate rate-control algorithms for a temperature-based, rate-modulated pacemaker.

An early attempt to respond to temperature, described in Fischell U.S. Pat. No. 3,867,950, involved measurement of body temperature. The pulse generating circuitry in the pacemaker was designed such that the output pulse rate would vary as a function of battery voltage and also as a function of body temperature as measured at the pacemaker case. A capacitor having a high temperature coefficient was used for temperature sensing, and the pacemaker's response to temperature was a fixed response corresponding to the temperature characteristics of the capacitor.

In German patent application No. 2609365, Csapo suggested the alternative use of either central body temperature or central blood temperature as a suitable parameter for the control of heart rate. The application discloses a temperature sensor lodged in the heart and connected as a base resistor in a blocking oscillator of the pulse generator to control the oscillator frequency and thereby the heart rate as a fixed function of instantaneous temperature. As with the Fischell pacemaker, variations in pacing rate with the proposed Csapo pacemaker would be solely dependent on the temperature characteristic of a selected hardware component, in this case a selected thermistor or other temperature sensor serving as the base resistor. Changes in central blood temperature during exercise were also the subject of a study reported by Csapo et al. in an article entitled "Auto-Regulation of Pacemaker Rate by Blood Temperature," presented at the VIII World Congress of Cardiology in Tokyo Japan, Sept. 17-23, 1978. Csapo et al. suggested in this article that the central blood temperature should regulate the heart rate along an S-curve, and the article includes a graph of an S-curve relationship between heart rate and temperature and also an equation, $HR = 81 + 21 \tang (2X - 71.2)$.

In Cook et al. U.S. Pat. Nos. 4,436,092 and 4,543,954, defined specific algorithms for a temperature-based exercise-responsive cardiac pacemaker. An important teaching of these patents is that the rate of change of temperature, as opposed to the instantaneous temperature, can be used as an indicator of exercise. Another important teaching is that cardiac rate may be calculated as a combination of rate components which individually vary in response to temperature conditions. In the preferred embodiments of the inventions described in these patents, venous blood temperature in the right ventricle of the heart is measured and processed according to an algorithm which represents the mathematical function between right ventricular blood temperature and heart rate in a normally functioning heart.

It is now known that two major mechanisms related to metabolic activity produce significant changes in blood temperature. The first is an increase in blood temperature due to increased metabolism and therefore heat generation during physical activity or emotional stress. The rate of rise is partly dependent upon workload. When the increased metabolism ceases, temperature returns to resting levels. The second mechanism producing a significant change in blood temperature is the response to the onset of activity or anticipation thereof resulting in an abrupt decrease in temperature. This is due to vasoactivity and blood flow redistribution to the cooler peripheral skeletal muscles and skin. An algorithm responsive to the initial drop in temperature was reported by Sellers et al. in the March-April, 1985 edition of *Pace* magazine, in a poster abstract entitled "Central Venous Temperature Profiles for a Pacemaker Algorithm." Subsequently, another algorithm responsive to the initial drop in temperature was disclosed in Alt et al. U.S. Pat. No. 4,719,920. The algorithm in the Alt et al. pacemaker appears to recognize an exercise-induced temperature dip on the basis of the current operating state of the pacemaker and three threshold-based criteria.

The blood temperature response caused by the above-mentioned major mechanisms may be separated into several components to produce a normal heart rate response. One component is the baseline resting temperature ($T_0$) which is the temperature of the patient at rest. Resting temperature varies with time of day, baseline metabolic state, and thermoregulatory balance. Another component is the temperature change with respect to the baseline temperature ($\Delta T$), which increases as activity continues and current temperature rises. A third component is the rate of temperature change ($dT/dt$ or ($\Delta T/\Delta t$), i.e., the temperature change in a given interval, whether a fixed time interval or some other interval such as a cardiac cycle. Positive values of this component have been shown to be related to work load and oxygen uptake under certain conditions. Certain combinations of particular temperature-based rate components are disclosed in the aforementioned Cook et al. patents and combinations of similar components are incorporated into commercially available pacemakers such as the Kelvin ® 500 pacemaker available from Cook Pacemaker Corporation of Leechburg, Penn.

The Kelvin ® 500 uses the rate of change of temperature, either alone or in conjunction with relative temperature rise above a moving baseline, to identify exercise. The baseline represents resting temperature and is calculated as the second minimum sample of eight temperature samples equally spaced in time, preferably over approximately a two-hour period. When the algorithm determines a significant change from baseline, representing exercise onset, pacing rate is adjusted starting from a programmable base rate. Temperature decrease at the onset of exercise causes pacing rate to increase gradually to a programmed intermediate rate which is maintained for a programmed period of from 2 to 10 minutes. When temperature starts to increase, confirming exercise, the pacemaker algorithm overrides the intermediate rate and gradually increases rate to a programmed upper rate. The algorithm can independently increase heart rate based solely on the rise in temperature if no drop occurs, or based solely on the drop in temperature if no rise occurs, or combinations thereof. The sensitivity of the algorithm to temperature changes and to the rate of rise or fall of temperature is programmable. The algorithm detects the decrease in temperature after peak exercise and decreases heart rate gradually to a programmed lower rate. Pacing rate is changed by incrementing or decrementing the R-to-R interval in steps of 20, 40 or 60 milliseconds, with the ability to further adjust the rate of pacing rate changes by programming either 5 or 10 seconds as the time interval between the step changes in pacing rate. Positive and negative rates of change of temperature are separately compared against a threshold value to determine the presence or absence of an exercise state. In the case of a positive rate of change of temperature, a value proportional thereto is added to a value proportional to the temperature rise above baseline, and pacing rate is incremented if the sum exceeds the threshold. In the case of a negative rate of change of temperature, a value proportional thereto (by a different scale factor than for the positive rate of change) is compared directly to the threshold.

Threshold detection is also the manner in which the initial dip in temperature at the onset of exercise is processed in the above-referenced Alt et al. pacemaker. More specifically, as described in the Alt et al. patent, the pacemaker employs several threshold-based criteria for interpreting a drop in a patient's central venous blood temperature as indicative of the commencement of exercise by a patient: (1) the absolute drop must exceed a certain minimum amount in the range of 0.12° to 0.25° C., (2) the time rate of change of the drop ($\Delta T/\Delta t$) must exceed a predetermined threshold slope, preferably in the range of from 0.12° to 0.20° C. per minute, and (3) the patient's heart rate must not exceed a predetermined threshold, preferably 85 beats per minute. At least the first two thresholds may be selected for a particular patient. The pacemaker's response to commencement of exercise is to abruptly increase stimulation rate by a step increase of selected magnitude, and to maintain that higher rate for a predetermined period of time followed by gradual reversion back toward the original rate. The magnitude of the drop and the magnitude of the rate of change of temperature are of no further significance. It is apparently only the relative magnitude of each, i.e., the magnitude relative to a threshold, as opposed to the absolute magnitude, which is considered useful by Alt et al. as a factor in setting pacing rate.

Significant progress has been made in temperature-based, rate modulation, but the known algorithms are still subject to improvement in the form of a more rapid and accurate algorithm more closely resembling the normal heart response to a variety of desirable and undesirable conditions experienced by pacemaker patients.

SUMMARY OF THE INVENTION

According to one aspect of the present invention, there is provided a temperature-based, rate-modulated cardiac therapy device having means for sensing blood temperature and processing means coupled to the sensing means for calculating cardiac rate as a function of temperature conditions. The processing means includes means for increasing cardiac rate by an amount proportional to the magnitude of a dip in blood temperature. The temperature dip is not merely compared against a threshold for purposes of determining which of two states a corresponding rate component should assume; instead, the rate component corresponding to the dip is proportional to the magnitude of the dip. The algorithm disclosed herein provides an earlier increase in cardiac rate than that provided by prior art devices which wait for the dip to exceed a threshold, and the rate increase itself, rather than being a fixed step or series of steps, varies in a physiologic manner as a direct function of the dip magnitude.

Another aspect of the present invention relates to a temperature-based, rate-modulated cardiac therapy device having means for sensing blood temperature, means coupled to the sensing means for determining first, second and third moving baseline temperatures, and processing means coupled to the sensing means for calculating cardiac rate, wherein the processing means includes summing means for obtaining a weighted sum of a plurality of the following rate components:

(1) the magnitude of a decrease in temperature below the first moving baseline temperature;

(2) the magnitude of an increase in temperature above the second moving baseline temperature;

(3) the magnitude of an increase in the first moving baseline temperature above the third moving baseline temperature; and (4) the absolute value of the rate of change of temperature.

According to another aspect of the present invention, there is provided a temperature-based, rate-modulated cardiac therapy device having means for sensing venous blood temperature and processing means coupled to the sensing means for calculating cardiac rate, wherein the processing means includes means for distinguishing between positive and negative rates of change of temperature, means for calculating a first rate component proportional to the magnitude of a negative rate of change of temperature, means for calculating a second rate component proportional to the magnitude of a positive rate of change of temperature, and means for increasing cardiac rate by the first and second rate components.

According to yet another aspect of the present invention, a temperature-based, rate-modulated cardiac therapy device has means for sensing venous blood temperature including means for producing a plurality of temperature values per minute, and processing means coupled to the sensing means for calculating cardiac rate in response to diurnal variations and deviations from resting temperature. The processing means includes means for deriving a daily minimum temperature from temperature values produced from a temperature history including, for example, an average minimum temperature over at least a 24-hour period, means for detecting temperature deviations from the daily minimum temperature, means for deriving a resting temperature from temperature values produced over an interval less than approximately 12 hours, means for detecting temperature deviations from the resting temperature, and means for combining the temperature deviations.

According to still yet another aspect of the present invention, a rate-modulated cardiac therapy device, such as a defibrillator, has a sensor for sensing a physiological state of which blood temperature is indicative for determining an appropriate cardiac therapy. Such therapy is advantageously utilized in a treatment for cardioversion or tachyarrhythmia. Blood temperature is periodically sensed and stored for creating a plurality of indicia. A processor then advantageously determines a cardiac therapy including at least one of plurality of rate components which is a function of at least one of a plurality of factors. These factors include, amongst others, a daily minimum temperature, a resting temperature, a rate of change of temperature, a dip in temperature, etc.

It is a general object of the present invention to provide an improved temperature-based, rate-modulated cardiac therapy device and method.

Another object is to respond to a variety of commonly encountered conditions in a manner more closely resembling that of a healthy heart.

Another object is to obtain more accurate and rapid response to temperature conditions warranting changes in cardiac output.

A further object of the present invention is to provide improved response to a drop in temperature and to the rate of change of temperature.

Related objects and advantages of the present invention will be apparent to those skilled in the art from the following description and accompanying drawings.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. The preferred embodiment is described in the context of a pacemaker application, but it is contemplated that the principles of the invention will also be applicable to other devices for cardiac therapy, such as artificial hearts and implantable cardioverter/defibrillators.

In the preferred embodiment of the present invention, the heart pacing rate is generally composed of components derived from the positive and negative rate of change of temperature, the magnitude of the temperature dip from baseline, the magnitude of the increasing temperature above the minimum temperature during exercise, and the difference between the baseline temperature and the daily minimum temperature. More specifically, a target pacing rate is formulated from incremental contributions derived from the above factors and added to a base heart rate. It is important to understand that the preferred embodiment of the present invention is capable of calculating (1) a rate component proportional to a positive rate of change of temperature, (2) a rate component proportional to the additive inverse of a negative rate of change of temperature, and (3) a rate component proportional to the magnitude of a dip in temperature. The rates of change of temperature and the temperature dip are not merely compared against a threshold for purposes of determining which of two states a particular rate component should assume; instead, the rate components are each proportional to the magnitude of their respective temperature parameter.

Figure 1:
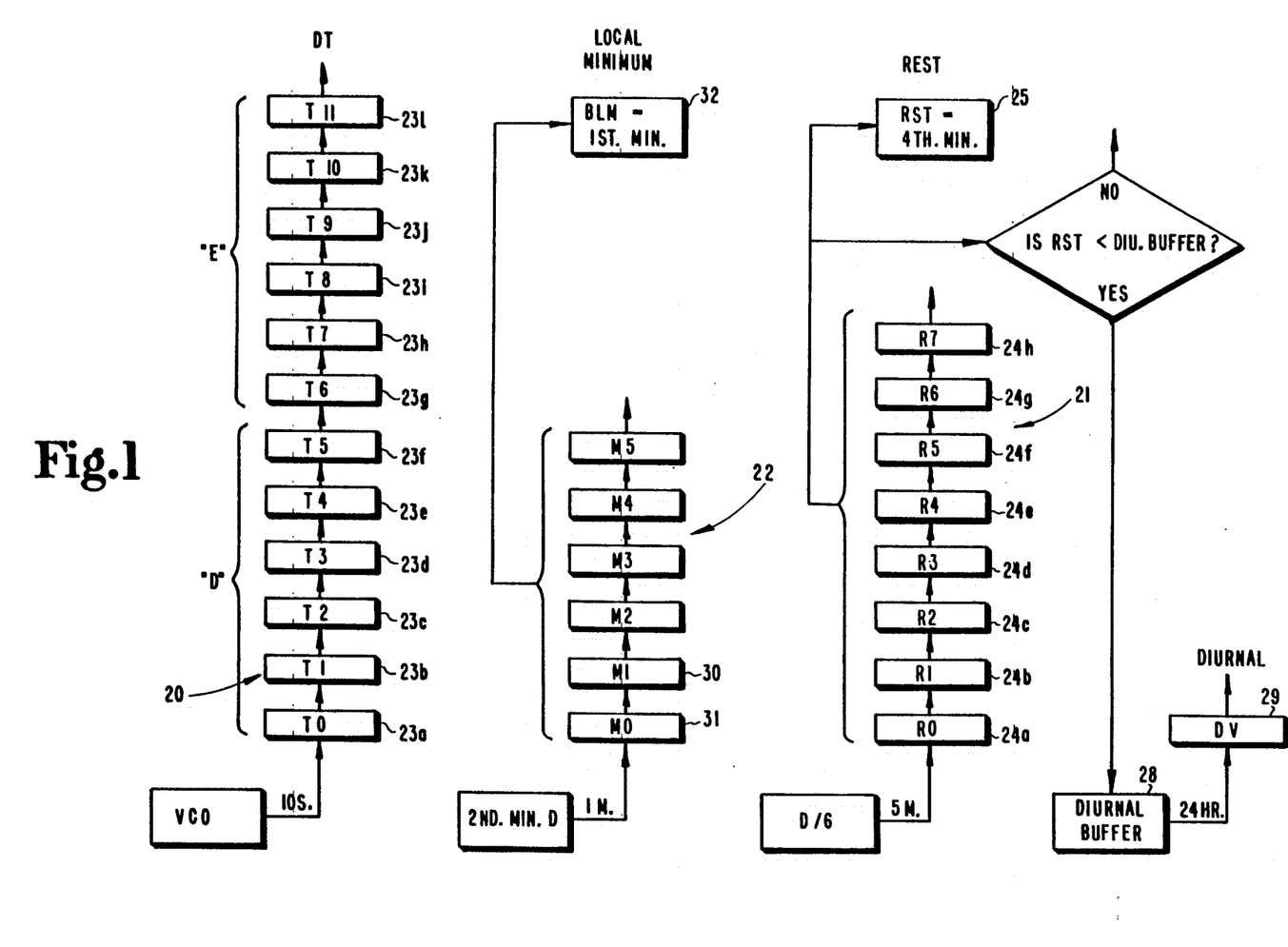
FIG. 1 is a block diagram of the various buffers and shift registers used in deriving rate components according to the preferred embodiment of the present invention.

Referring more specifically to FIG. 1, the data buffers which are used in the calculation of heart rate according to the present invention are disclosed. These data buffers include temperature (T) buffer 20, baseline resting temperature (R) buffer 21 and minimum value (M) buffer 22. The rate of change of temperature is calculated using 12 temperature samples taken at 10-second intervals and then stored in temperature buffer 20 in condensed or compact form. The rate of change of temperature is the sum of the six most recent temperature readings in temperature buffer 20 minus the sum of the six oldest temperature readings in temperature buffer 20. The calculation of rate of change using two minutes of data eliminates the effect of the one-cycle-per-minute variations in temperature recorded during deep rest. T buffer 20 includes twelve shift registers 23a–23l which roll over (rotate) every ten seconds so as to retain a sequential train of the twelve most recent blood temperature readings, designated as T0 through T11 respectively. The current T0 value is shifted into register 23b as a new T1 value, the current T1 value is shifted into register 23c as a new T2 value, and so on, with the old T11 value being discarded, and the newest temperature reading is loaded into register 23a as a new T0 value.

Figure 2:
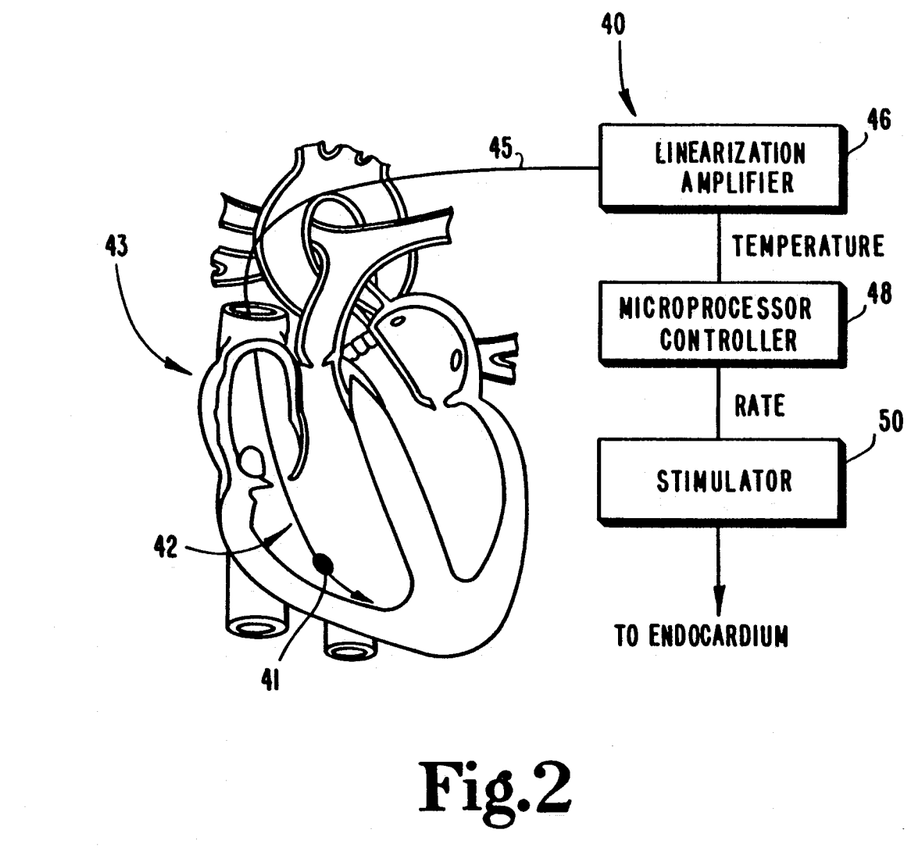
FIG. 2 is a block diagram of the hardware components of the preferred embodiment of the present invention, illustrated in operational relationship with a human heart.

FIG. 2 shows the temperature-responsive pacemaker 40 of the present invention in block diagram form. Thermistor 41 is centrally located within the right ventricle 42 of the heart 43 and electrically connected via pacing/sensing lead 45 to a linearization amplifier 46 which linearizes the output of the thermistor versus temperature over the temperature range encountered in the right ventricle. The linearized thermistor output signal is coupled to a microprocessor controller 48 in which individual values of the output signal are periodically converted from analog to digital and then stored in the T buffer described above. Microprocessor controller 48 includes a microprocessor which processes the temperature data according to an algorithm described in detail herein. Microprocessor controller 48 is connected to a pulse generator 50 which supplies pulses on demand to the endocardium of the patient's right ventricle 42 at a rate determined by software in the microprocessor. The pulse generator and the manner of supplying pulses to the heart for electrical stimulation thereof, as well as techniques for sensing natural ventricular contractions and pacing on demand, are well known to those skilled in the art. One suitable lead for temperature-based, demand pacing is disclosed in U.S. Pat. No. 4,543,954.

The six most recent readings (T0–T5) are totalled and their sum designated as quantity D. The six oldest readings still in the T buffer (T6–T11) are totalled and their sum designated as quantity E. The difference, D−E, represents the rate of change of temperature, or the derivative. If D≧E, such as occurs during a rise in temperature, one coefficient (tau 2) is multiplied by the rate of change (D−E) in order to obtain an incremental heart rate component (DT) to be added t other components of the heart rate. This rate component is directly proportional to the magnitude of the rate of change of temperature. If the rate of change of temperature is negative, i.e., D<E, such as occurs during the dip in temperature at the onset of exercise, a second coefficient (tau 1) is multiplied by the additive inverse of the rate of change of temperature, i.e., E−D. The resulting rate component is directly proportional to the additive inverse of the rate of change of temperature, and is added to other components of the heart rate in a manner which will be explained in detail. A heart rate calculation is executed each time a temperature sample is taken, that is, every 10 seconds.

To calculate the magnitude of the temperature dip at the beginning of exercise, the average (D/6) of the six most recent temperature samples from the temperature buffer is saved and stored at fixed intervals in resting buffer 21. Resting buffer 21 has a total of eight registers 24a–24h, and each new value is loaded into register 24a as value R0. The storage interval is presently set at between one and five minutes. As the R buffer rotates, the R0 value shifts to the R1 register 24b allowing another D/6 value to be entered into register 24a. The fourth rank (fourth minimum) value of the R buffer is used as the baseline resting temperature (RST), represented by block 25 in FIG. 1. It will be appreciated from the repetitive nature of the RST calculation that resting temperature is a moving baseline. The magnitude of the dip is the resting baseline temperature RST minus the average D/6 of the six most recent temperature values, which is a positive quantity for a decrease in temperature. The magnitude of the dip is multiplied by a coefficient tau 5 to produce another incremental contribution (STX) to the heart rate. Negative values of STX are disregarded, but positive values are added to the target rate (TR).

An additional rate component providing an incremental contribution to heart rate is the increase in current temperature over the minimum temperature during exercise, a local minimum which has been found to be another useful moving baseline. This rate component is calculated with the aid of M buffer 22, a six-value buffer. At fixed intervals of from one to five minutes, the second rank (second minimum) value of the six most recent temperature samples (T0–T5) in temperature buffer 20 is stored as a new M0 in register 31 of M buffer 22. The old M0 value becomes the new M1 value, and so on, with the old M5 value being discarded. The first minimum value in the M buffer is obtained and used as a baseline local minimum, represented as BLM in block 32 of FIG. 1. The difference between the value M0 and the value BLM represents the accumulated rise in present temperature above local minimum. The quantity M0−BLM is multiplied by another coefficient (tau 3), and the product, if non-negative, is used as another incremental contribution (TXB) to the heart rate. The local minimum is preferably calculated over a smaller interval than the resting temperature. One example of this is depicted in FIG. 1, in which BLM is calculated at one-minute intervals whereas RST is calculated at five-minute intervals.

Another incremental contribution to heart rate is derived from the difference between baseline resting temperature (RST) and a daily minimum temperature (DV). This rate component is included to provide proper response to diurnal variations in blood temperature and, correspondingly, normal heart rate. Resting baseline temperatures are compared to find the minimum for a 24-hour period. More specifically, the baseline resting temperature value (RST) is compared with the value in diurnal buffer 28 each time a new RST value is derived. If RST is less than the temperature value in diurnal buffer 28, the lower value is loaded into the diurnal buffer in place of the previous value. If not, the diurnal buffer is unchanged. Every 24 hours the current value in diurnal buffer is saved as value DV, represented by block 29 in FIG. 1, and the diurnal buffer is reinitialized to find a new minimum resting temperature for the next 24 hours. The value DV is subtracted from the current resting baseline temperature (RST) for each new cardiac rate calculation and multiplied by another coefficient (tau 4) to provide another incremental contribution (DIU) to heart rate. Negative values of DIU are disregarded, but positive values are added to the target rate. The value DV represents a third moving baseline temperature in addition to the first and second moving baseline temperatures RST and BLM. If desired, yet another moving baseline may be created by incorporating a continually moving 24-hour window into the DV calculation.

The target pacing rate is formulated from all the incremental contributions explained above which are added to a base heart rate defined by a lower rate limit (LR). Each contribution when non-zero is a positive contribution to rate. The new rate (NR) is calculated from the target rate (TR) and the previous rate (PR). The pacemaker also includes an upper rate (UR) limit, as will be described. The rate calculation is performed according the following equations and conditional branching instructions which are incorporated into software in the pacemaker:

| | |
|---|---|
| (1) STX = tau 5 × (RST − D/6) | Dip Magnitude |
| (2) if STX < 0 then STX = 0 | |
| (3) TR = LR + STX | |
| (4) DIU = tau 4 × (RST − DV) | Diurnal Variation |
| (5) if DIU < 0 then DIU = 0 | |
| (6) TR = TR + DIU | |
| (7) TXB = tau 3 × (M0 − BLM) | Deviation from Local Min. |
| (8) if TXB < 0 then TXB = 0 | |
| (9) IF D < E then: | Negative dT/dt |
| (10) DT = tau 1 × (E − D) | |
| (11) TR = TR + DT | |
| (12) if TR > IR then TR = IR | |
| (13) TR = TR + TXB | |
| (14) if TR > UR then TR = UR | |
| (15) IF D ≥ E then: | Positive (or zero) dT/dt |
| (16) DT = tau 2 × (D − E) | |
| (17) if TR > IR then TR = IR | |
| (18) TR = TR + DT + TXB | |
| (19) if TR > UR then TR = UR | |
| (20) NR = (PR + TR)/2 | Rate Smoothing |

The above equations are set forth in programming language in a conventional manner whereby the variable on the left side of the equation is set equal to the value of the expression on the right side, which expression may include a prior value of the variable being calculated. For example, upon execution of equation 6, target rate TR is set equal to the then-current value of TR plus the then-current value of DIU, thus creating a new TR value. Target rate is thus incremented in stages during each calculation of a new heart rate. It will be understood that the condition in conditional branching instruction 9 must be satisfied for instructions 10–14 to be executed, and that instruction 15 similarly controls the execution of instruction 16–19.

Rates are limited so as to provide demand pacing within a desired range of pacing rates. Therefore, pacing rates vary between the base pacing rate (LR) and the maximum pacing rate (UR) under all conditions. In addition, an intermediate rate (IR) limit is applied to a subset or subtotal of components including the sum LR+STX+DIU. In the case of a negative value of dT/dt, the value DT is added to the above sum before limiting TR to IR if necessary (instructions 11 and 12).

Otherwise the above sum is limited to IR, if necessary, prior to adding DT (instructions 17 and 18). TXB, the deviation from local minimum, is added to target rate after the intermediate rate limiting, such that it may cause target rate to exceed the intermediate limit, but never the upper limit.

In order to avoid abrupt changes in pacing rate, a limitation on the slew rate or rate of change of pacing rate is also provided in the preferred embodiment. The algorithm repetitively sets the new heart rate equal to the average of a newly calculated target rate and the actual previous heart rate, thereby smoothing rate fluctuations, as depicted in equation 20. Thus, heart rate increases (and decreases) by half the difference between the target rate and the current rate. Greater or lesser proportions of the difference between TR and PR for each change in pacing rate may be implemented as desired.

In addition, further limits for incrementing and decrementing the pacing rates are selected by the physician. By way of example, an incrementing rate limit in the range of 12 to 60 pulses per minute per minute and a decrementing rate limit in the range of 6 to 30 pulses per minute per minute to further limit the rate of change in the cardiac pacing rate are selectable by the physician.

It is to be understood that the values of tau 1 through tau 5 are selected for the particular subject for which the device of the present invention is to be used. The following table specifies preferred values for the five coefficients for various gain values, or response characteristics, of the pacemaker. Variations of one or more of these coefficients, either in absolute terms or relative to each other, may be made if desired for a particular subject without departing from the scope of the present invention.

| | COEFFICIENTS FOR TAU 1 THROUGH TAU 5 | | | | | | | | | |
|---|---|---|---|---|---|---|---|---|---|---|
| | GAIN | | | | | | | | | |
| | Minimal | | | Nominal | | | | Maximal | | |
| Tau | 1 | 2 | 3 | 4 | 5 | 6 | 7 | 8 | 9 | 10 |
| 1 | .011 | .013 | .016 | .020 | .025 | .031 | .039 | .047 | .059 | .070 |
| 2 | .059 | .070 | .094 | .109 | .141 | .172 | .203 | .250 | .313 | .375 |
| 3 | .234 | .281 | .375 | .438 | .563 | .688 | .813 | 1.00 | 1.25 | 1.50 |
| 4 | .055 | .055 | .055 | .055 | .055 | .055 | .055 | .055 | .055 | .055 |
| 5 | .203 | .234 | .281 | .375 | .438 | .563 | .688 | .813 | 1.00 | 1.25 |

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. For example, the cardiac therapy device may include a sensor for sensing a physiological state such as a blood temperature sensor for determining an appropriate therapy for abnormal conditions such as cardioversion or tachyarrhythmia. The physiological state sensor may also provide hemodynamic assessment for medical personnel in treating such abnormal conditions. The sensor may be further utilized for the automatic release of medication or for determining metabolism in providing defibrillation. Temperature is utilized to discriminate between various physiological states or conditions in providing appropriate cardiac therapy. Temperature is periodically sensed and stored for creating indicia thereof. A processor then determines an appropriate therapy including at least one rate component which is a function of at least one of a plurality of factors. These factors, as previously discussed, include a daily minimum temperature, a resting temperature, rate of change of temperature, etc. For more detailed determinations the processor derives one or more additional components from these factors.

What is claimed is:

1. A temperature-based, rate-modulated cardiac therapy device, comprising:
   means for sensing central venous blood temperature; and
   processing means coupled to said sensing means for calculating cardiac rate as a function of temperature conditions, one of said conditions including a dip in central venous blood temperature at the onset of exercise, said processing means including
   means for calculating a first rate component proportional to the magnitude of said dip; and
   means for increasing cardiac rate by said first rate component.

2. The cardiac therapy device of claim 1 wherein said processing means further includes
   means for calculating a second rate component proportional to the absolute value of the rate of change of temperature; and
   means for increasing cardiac rate by said second rate component in addition to said first rate component.

3. The cardiac therapy device of claim 2 wherein said second rate component calculating means includes means for calculating said second rate component with one scale factor for a negative rate of change of temperature and with a greater scale factor for a positive rate of change of temperature.

4. The cardiac therapy device of claim 3 wherein said processing means further includes
   means for deriving a local minimum temperature;
   means for calculating a third rate component proportional to an increase in temperature above said local minimum temperature; and
   means for increasing cardiac rate by said third rate component in addition to said first and second rate components.

5. The cardiac therapy device of claim 4 wherein said processing means further includes
   means for deriving a resting temperature;
   means for deriving a daily minimum temperature;
   means for calculating a fourth rate component proportional to an increase in said resting temperature above said daily minimum temperature; and
   means for increasing cardiac rate by said fourth rate component in addition to said first, second and third rate components.

6. The cardiac therapy device of claim 5 wherein said first rate component is proportional to said resting temperature minus current temperature;
   said third rate component is proportional to current temperature minus said local minimum temperature;
   said fourth rate component is proportional to said resting temperature minus said daily minimum temperature; and
   wherein said processing means includes means for inhibiting response to negative values of said first, third and fourth rate components.

7. The cardiac therapy device of claim 6 further comprising smoothing means for limiting the rate of change of cardiac rate, said smoothing means including means for limiting the change in cardiac rate during a predetermined interval to a fraction of the cardiac rate change calculated by said processing means.

8. The cardiac therapy device of claim 7 further comprising rate limit means for limiting the cardiac rate increase in stages during calculation thereof.

9. The cardiac therapy device of claim 1 wherein said processing means further includes
   means for deriving a local minimum temperature;
   means for calculating a second rate component proportional to an increase in temperature above said local minimum temperature; and
   means for increasing cardiac rate by said second rate component in addition to said first rate component.

10. The cardiac therapy device of claim 1 wherein said processing means further includes
    means for deriving a resting temperature;
    means for deriving a daily minimum temperature;
    means for calculating a second rate component proportional to an increase in said resting temperature above said daily minimum temperature; and
    means for increasing cardiac rate by said second rate component in addition to said first rate component.

11. The cardiac therapy device of claim 1 wherein said processing means further includes
    means for deriving a resting temperature; and
    means for inhibiting response to a negative value of said first rate component;
    wherein said first rate component is proportional to said resting temperature minus current temperature.

12. The cardiac therapy device of claim 1 further comprising smoothing means for limiting the rate of change of cardiac rate, said smoothing means including means for limiting the change in cardiac rate to a fraction of the cardiac rate change calculated by said processing means.

13. A temperature-based, rate-modulated cardiac therapy device, comprising:
    means for sensing blood temperature; and
    processing means coupled to said sensing means for calculating cardiac rate, said processing means including means for increasing cardiac rate by an amount proportional to the magnitude of a dip in blood temperature.

14. The cardiac therapy device of claim 13 wherein said processing means further includes means for increasing cardiac rate by an amount proportional to the absolute value of the rate of change of temperature.

15. The cardiac therapy device of claim 14 wherein said processing means further includes means for calculating a cardiac rate increase with one scale factor for a negative rate of change of temperature and with a greater scale factor for a positive rate of change of temperature.

16. The cardiac therapy device of claim 15 wherein said processing means further includes
    means for deriving a local minimum temperature; and
    means for increasing cardiac rate by an amount proportional to an increase in temperature above said local minimum temperature.

17. The cardiac therapy device of claim 16 wherein said processing means further includes
    means for deriving a resting temperature;
    means for deriving a daily minimum temperature; and
    means for increasing cardiac rate by an amount proportional to an increase in said resting temperature above said daily minimum temperature.

18. The cardiac therapy device of claim 13 wherein said processing means further includes
means for deriving a local minimum temperature; and
means for increasing cardiac rate by an amount proportional to an increase in temperature above said local minimum temperature.

19. The cardiac therapy device of claim 13 wherein said processing means further includes
means for deriving a resting temperature;
means for deriving a daily minimum temperature;
means for increasing cardiac rate by an amount proportional to an increase in said resting temperature above said daily minimum temperature.

20. The cardiac therapy device of claim 13 wherein said processing means further includes means for increasing cardiac rate by an amount proportional to a positive rate of change of temperature.

21. The cardiac therapy device of claim 20 wherein said processing means further includes means for increasing cardiac rate by an amount proportional to the additive inverse of a negative rate of change of temperature.

22. The cardiac therapy device of claim 21 wherein said processing means further includes
means for deriving a local minimum temperature; and
means for increasing cardiac rate by an amount proportional to an increase in temperature above said local minimum temperature.

23. The cardiac therapy device of claim 22 wherein said processing means further includes
means for deriving a resting temperature;
means for deriving a daily minimum temperature; and
means for increasing cardiac rate by an amount proportional to an increase in said resting temperature above said daily minimum temperature.

24. A temperature-based, rate-modulated cardiac therapy device, comprising:
means for sensing blood temperature;
means coupled to said sensing means for determining first, second and third moving baseline temperatures; and
processing means coupled to said sensing means for calculating cardiac rate, said processing means including summing means for obtaining a weighted sum of a plurality of the following rate components:
the magnitude of a decrease in temperature below said first moving baseline temperature;
the magnitude of an increase in temperature above said second moving baseline temperature;
the magnitude of an increase in said first moving baseline temperature above said third moving baseline temperature; and
the absolute value of the rate of change of temperature.

25. The cardiac therapy device of claim 24 wherein said determining means includes means for calculating said first, second and third moving baseline temperatures periodically from temperature measurements taken over first, second and third intervals, respectively, said first interval exceeding said second interval in length, said third interval exceeding said first interval in length.

26. The cardiac therapy device of claim 25 wherein said determining means includes rank filter means for ranking multiple temperature values and selecting a value of predetermined rank therefrom.

27. The cardiac therapy device of claim 26 further comprising smoothing means for limiting the rate of change of cardiac rate, said smoothing means including means for limiting a change in cardiac rate during a predetermined interval to a fraction of the difference between current cardiac rate and a new cardiac rate calculated by said processing means.

28. The cardiac therapy device of claim 27 further comprising means for determining a lower rate limit, wherein said summing means includes means for adding said weighted sum to said lower rate limit.

29. A temperature-based, rate-modulated cardiac therapy device, comprising:
means for sensing venous blood temperature; and
processing means coupled to said sensing means for calculating cardiac rate, said processing means including
means for distinguishing between positive and negative rates of change of temperature;
means for calculating a first rate component proportional to the magnitude of a negative rate of change of temperature;
means for calculating a second rate component proportional to the magnitude of a positive rate of change of temperature; and
means for increasing cardiac rate by said first and second rate components.

30. The cardiac therapy device of claim 29 further comprising means for storing first and second scale factors for said first and second rate component calculating means, respectively, said second scale factor being greater than said first scale factor.

31. The cardiac therapy device of claim 29 wherein said processing means further includes means for periodically executing a cardiac rate calculation; and
wherein said means for increasing cardiac rate is responsive to only one of said first and second rate components during each cardiac rate calculation.

32. The cardiac therapy device of claim 31 wherein said means for increasing cardiac rate includes means for alternatively adding said first and second rate components to a subtotal of other rate components;
further comprising rate limit means for limiting the effect of said first and second rate components, said rate limit means including
means responsive to a negative rate of change of temperature for limiting the sum of said subtotal and said first rate component to a predetermined intermediate rate limit value; and
means responsive to a positive rate of change of temperature for limiting said subtotal to said intermediate rate limit value before said second rate component is added.

33. The cardiac therapy device of claim 29 wherein said means for increasing cardiac rate includes means for alternatively adding said first and second rate components to a subtotal of other rate components;
further comprising rate limit means for limiting the effect of said first and second rate components, said rate limit means including
means responsive to a negative rate of change of temperature for limiting the sum of said subtotal and said first rate component to a predetermined intermediate rate limit value; and
means responsive to a positive rate of change of temperature for limiting said subtotal to said intermediate rate limit value before said second rate component is added.

34. A temperature-based, rate-modulated cardiac therapy device, comprising:
 means for sensing venous blood temperature, said sensing means including means for producing a plurality of temperature values per minute; and
 processing means coupled to said sensing means for calculating cardiac rate in response to diurnal variations and deviations from resting temperature, said processing means including
 means for deriving a daily minimum temperature from temperature values produced over a 24-hour period;
 means for detecting temperature deviations from said daily minimum temperature;
 means for deriving a resting temperature from temperature values produced over an interval less than approximately 12 hours;
 means for detecting temperature deviations from said resting temperature; and
 means for combining said temperature deviations.

35. The cardiac therapy device of claim 34 wherein said means for detecting temperature deviations from said daily minimum temperature includes means for detecting the magnitude of an increase in said resting temperature above said daily minimum temperature, and means for inhibiting response to a decrease in said resting temperature below said daily minimum temperature.

36. The cardiac therapy device of claim 35 further comprising:
 means for deriving a local minimum temperature from temperature values produced over an interval less than the interval for said resting temperature; and
 means for detecting the magnitude of an increase in temperature above said local minimum temperature, and means for inhibiting response to a decrease in temperature below said local minimum temperature;
 wherein said means for detecting temperature deviations from said resting temperature includes means for detecting the magnitude of a decrease in temperature below said resting temperature, and means for inhibiting response to an increase in temperature above said resting temperature.

37. The cardiac therapy device of claim 36 wherein said means for deriving a resting temperature includes means for deriving a resting temperature from temperature values produced over an interval of between approximately 8 and 40 minutes.

38. The cardiac therapy device of claim 37 wherein said means for deriving a daily minimum temperature includes means for comparing different values of said resting temperature.

39. A temperature-based method of modulating cardiac rate, comprising the steps:
 sensing blood temperature; and
 calculating a new cardiac rate in response to sensed blood temperature, said calculating step including increasing cardiac rate by an amount proportional to the magnitude of a dip in blood temperature.

40. The method of claim 39 wherein said calculating step further includes increasing cardiac rate by an amount proportional to a positive rate of change of temperature.

41. The method of claim 40 wherein said calculating step further includes increasing cardiac rate by an amount proportional to the additive inverse of a negative rate of change of temperature.

42. The method of claim 41 wherein said calculating step further includes
 deriving a local minimum temperature; and
 increasing cardiac rate by an amount proportional to an increase in temperature above said local minimum temperature.

43. The method of claim 42 wherein said calculating step further includes
 deriving a resting temperature;
 deriving a daily minimum temperature; and
 increasing cardiac rate by an amount proportional to an increase in said resting temperature above said daily minimum temperature.

44. The method of claim 39 wherein said calculating step further includes
 deriving a local minimum temperature; and
 increasing cardiac rate by an amount proportional to an increase in temperature above said local minimum temperature.

45. The method of claim 39 wherein said calculating step further includes
 deriving a resting temperature;
 deriving a daily minimum temperature; and
 increasing cardiac rate by an amount proportional to an increase in said resting temperature above said daily minimum temperature.

46. A temperature-based method of modulating cardiac rate, comprising the steps:
 sensing blood temperature;
 determining first, second and third moving baseline temperatures; and
 calculating a new cardiac rate in response to sensed blood temperature, said calculating step including obtaining a weighted sum of a plurality of the following rate components:
 the magnitude of a decrease in temperature below said first moving baseline temperature;
 the magnitude of an increase in temperature above said second moving baseline temperature;
 the magnitude of an increase in said first moving baseline temperature above said third moving baseline temperature; and
 the absolute value of the rate of change of temperature.

47. The method of claim 46 wherein said determining step includes calculating said first, second and third moving baseline temperatures periodically from temperature measurements taken over first, second and third intervals, respectively, said first interval exceeding said second interval in length, said third interval exceeding said first interval in length.

48. The method of claim 47 wherein said determining step includes ranking multiple temperature values and selecting a value of predetermined rank therefrom.

49. The method of claim 48 further comprising the step of limiting the rate of change of cardiac rate, said limiting step including limiting a change in cardiac rate during a predetermined interval to a fraction of the difference between current cardiac rate and a new cardiac rate calculated in said calculating step.

50. The method of claim 49 further comprising the step of determining a lower rate limit, wherein said calculating step includes adding said weighted sum to said lower rate limit.

51. A temperature-based, rate-modulated cardiac therapy device, comprising:

sensing means for sensing central venous blood temperature;

sampling means coupled to said sensing means for periodically creating indicia of central venous blood temperature;

at least one buffer means for storing a plurality of said indicia of central venous blood temperature;

processing means coupled to said at least one buffer means for determining a cardiac pacing rate including a first rate component which is a function of the dip in central venous blood temperature which occurs at the onset of exercise, said processing means including means for calculating said first rate component such that it is proportional to the magnitude of said dip in central venous blood temperature; and means for increasing the cardiac pacing rate by said at least one rate component.

52. The cardiac therapy device of claim 51, wherein said at least one buffer means stores a first predetermined number of indicia of central venous blood temperature during a first time period of a first predetermined duration, and a second predetermined number of indicia of central venous blood temperature during a second time period of a second predetermined duration, said first time period immediately preceding in time said second time period, said processing means including means for determining, based on the indicia stored in said first and said second time periods, a second rate component which is proportional to the absolute value of the rate of change of central venous blood temperature; and means for increasing cardiac rate by both of said first second rate components.

53. The cardiac therapy device of claim 52, wherein said second rate component which is proportional to the absolute value of the rate of change of central venous blood temperature is proportionally greater for a positive rate of change than for a negative rate of change.

54. The cardiac therapy device of claim 52, having a second buffer means, said second buffer means storing a plurality of said indicia of central venous blood temperature, said indicia being selected for storage in said second buffer means from said second predetermined number of indicia at a first periodic interval which is representative of a predetermined minimum value of said second predetermined number of indicia stored in said at least one buffer at the time said indicia is selected, one of said indicia stored in said second buffer being selected to represent a local minimum central venous blood temperature, said processing means including means for determining, based on said indicia representing a local minimum central venous blood temperature and on the indicia most recently selected for storage in said second buffer, a third rate component which is proportional to an increase in temperature above ,said local minimum central venous blood temperature, and means for increasing cardiac rate by said third rate component in addition to said first and second rate components.

55. The cardiac therapy device of claim 54, wherein said indicia selected for storage in said second buffer means from said second predetermined number of indicia, is the indicia representative of the second lowest central venous blood temperature, and said indicia stored in said second buffer selected to represent a local minimum temperature is the indicia representing the lowest central venous blood temperature.

56. The cardiac therapy device of claim 54, wherein said sampling means creates an indicia of central venous blood temperature at approximately ten second intervals, said first and second time periods are each of approximately one minute duration, and said first periodic interval is of from one to five minutes duration.

57. The cardiac therapy device of claim 56, wherein said second buffer means stores six of said indicia of central venous blood temperature.

58. The cardiac therapy device of claim 54, having a third buffer means and a fourth buffer means, said third buffer means storing a plurality of indicia representative of the average value of the indicia stored in said first buffer means during said second time period at a second periodic interval which is greater in duration than said first time period, one of said indicia stored in said third buffer means being selected to represent a resting central venous blood temperature, said fourth buffer means storing an indicia representative of the daily minimum central venous blood temperature, said indicia selected for storage in said fourth buffer being the indicia representing the lowest resting central venous temperature occurring during a third periodic interval of approximately twenty-four hours duration, the indicia stored in said fourth buffer at the end of said third period being used to represent the daily minimum central venous blood temperature for the next twenty-four hour period, said processing means including means for determining, based on said indicia representing the daily minimum central venous blood temperature and on said indicia representing the resting central venous blood temperature, a fourth rate component which is proportional to an increase in resting temperature above, said daily minimum central venous blood temperature, and means for increasing cardiac rate by said fourth rate component in addition to said first, second, and third rate components.

59. The cardiac therapy device of claim 58, wherein said first rate component is proportional to said resting central venous blood temperature minus said current central venous blood temperature, said third rate component is proportional to said current central venous blood temperature minus said local minimum central venous blood temperature, said fourth rate component is proportional to said resting central venous blood temperature minus said daily minimum central venous blood temperature, and said processing means includes means for inhibiting response to negative values of said first, said third, and said fourth rate components.

60. The cardiac therapy device of claim 59, wherein said processing means includes smoothing means for limiting the rate of change of cardiac rate, said smoothing means including means for limiting the change in cardiac rate during a fourth periodic interval to a portion of the cardiac rate change represented by the total of said first, second, third and fourth rate components.

61. The cardiac therapy device of claim 60, wherein said processing means includes rate limiting means, which limits the cardiac pacing rate to rates between a lower base pacing rate and an upper maximum pacing rate.

62. The cardiac therapy device of claim 58, wherein said processing means includes smoothing means for limiting the rate of change of cardiac rate, said smoothing means including means for limiting the change in cardiac rate during a fourth periodic interval to a portion of the cardiac rate change represented by the total of said first, second, third and fourth rate components.

63. The cardiac therapy device of claim 62, wherein said processing means includes rate limiting means, which limits the cardiac pacing rate to rates between a lower base pacing rate and an upper maximum pacing rate.

64. The cardiac therapy device of claim 58, wherein said processing means includes intermediate rate limiting means which limits the increase in cardiac rate due to said first, second, and fourth rate components to an intermediate rate for negative rates of change of central venous blood temperature, such that said cardiac rate is limited to said intermediate rate plus said third rate component.

65. The cardiac therapy device of claim 64, wherein said processing means includes smoothing means for limiting the rate of change of cardiac rate, said smoothing means including means for limiting the change in cardiac rate during a fourth periodic interval to a portion of the cardiac rate change represented by the total of said first, second, third and fourth rate components.

66. The cardiac therapy device of claim 65, wherein said processing means includes rate limiting means, which limits the cardiac pacing rate to rates between a lower base pacing rate and an upper maximum pacing rate.

67. The cardiac therapy device of claim 58, wherein said processing means includes intermediate rate limiting means which limits the increase in cardiac rate due to said first and fourth rate components to an intermediate rate for positive rates of change of central venous blood temperature, such that said cardiac rate is limited to said intermediate rate plus said second and third rate components.

68. The cardiac therapy device of claim 67, wherein said processing means includes smoothing means for limiting the rate of change of cardiac rate, said smoothing means including means for limiting the change in cardiac rate during a fourth periodic interval to a portion of the cardiac rate change represented by the total of said first, second, third and fourth rate components.

69. The cardiac therapy device of claim 68, wherein said processing means includes rate limiting means, which limits the cardiac pacing rate to rates between a lower base pacing rate and an upper maximum pacing rate.

70. The cardiac therapy device of claim 52, wherein said sampling means creates indicia of central venous blood temperature at approximately ten second intervals, and said first and second time periods are each of approximately one minute duration.

71. A temperature-based, rate-modulated cardiac therapy device, comprising:
    means for sensing venous blood temperature, said sensing means including means for producing a plurality of temperature values per minute; and
    processing means coupled to said sensing means for calculating cardiac rate in response to deviations between diurnal and resting temperatures, said processing means including
    means for deriving a daily minimum temperature from temperature values produced over a 24-hour period;
    means for deriving a resting temperature from temperature values produced over an interval less than approximately 12 hours; and
    means for deriving deviations between said daily minimum temperature and said resting temperature.

72. A temperature-based, rate-modulated cardiac therapy device, comprising:
    first sensing means for sensing a physiological state, said first sensing means including second sensing means for sensing venous blood temperature;
    sampling means coupled to said first sensing means for periodically creating indicia of said blood temperature;
    at least one buffer means for storing a plurality of said indicia of said blood temperature;
    processing means coupled to said at least one buffer means for determining a cardiac therapy including a first rate component which is proportional to the magnitude of a dip in said blood temperature.

73. The device of claim 72 wherein said processing means include means for deriving a second rate component which is a function of at least one of a plurality of factors including a daily minimum temperature, a resting temperature, a rate of change of temperature, an absolute value of said rate of change of temperature, a local minimum temperature, and a weighted sum of a number of factors.

* * * * *